United States Patent [19]
Morgan et al.

[11] Patent Number: 5,945,326
[45] Date of Patent: Aug. 31, 1999

[54] METHOD FOR CLONING AND PRODUCING THE SPEL RESTRICTION ENDONUCLEASE

[75] Inventors: Richard D. Morgan, Middleton; Zhiyuh Chang, Beverly; Fana B. Mersha, Somerville, all of Mass.

[73] Assignee: New England Biolabs, Inc., Beverly, Mass.

[21] Appl. No.: 08/821,619

[22] Filed: Mar. 20, 1997

[51] Int. Cl.$^6$ .............................. C12N 9/22; C12N 15/55
[52] U.S. Cl. .................. 435/199; 435/320.1; 435/252.3; 536/23.2
[58] Field of Search ................. 435/199, 320.1, 435/252.3; 536/23.2

[56] References Cited

U.S. PATENT DOCUMENTS

| | | | |
|---|---|---|---|
| 5,200,333 | 4/1993 | Wilson | 435/172.3 |
| 5,320,957 | 6/1994 | Brooks et al. | 435/172.3 |
| 5,340,733 | 8/1994 | Ueno et al. | 435/199 |
| 5,492,823 | 2/1996 | Xu | 435/194 |
| 5,532,153 | 7/1996 | Xu et al. | 435/199 |
| 5,543,308 | 8/1996 | Morgan et al. | 435/172.3 |

OTHER PUBLICATIONS

Roberts, R.J. (1985) Nucl. Acids Res. r165, r187.
Kosykh, et al., Molec. Gen. Genet., 178:717–719 (1980).
Mann, et al., Gene, 3:97–112 (1978).
Walder, et al., Proc. Nat. Acad. Sci., 78:1503–1507 (1981).
Bougueleret, et al., Nucl. Acid Res., 12:3659–3676 (1984).
Gingeras and Brooks, Proc. Natl. Acad. Sci. USA 80:402–406 (1983).
Theriault and Roy, Gene, 19:355–359 (1982).
Blumenthal, et al., J. Bacteriol., 164:501–509 (1985).
Kiss, et al., Nucl. Acid Res., 13:6403–6421 (1985).
Szomolanyi, et al, Gene, 10:219–225 (1980).
Janulaitis, et al., Gene, 20:197–204 (1982).
Kiss and Baldauf, Gene, 21:111–119 (1983).
Walder, et al., (J. Biol. Chem., 258:1235–1241 (1983).
Piekarowicz, et al., Nucleic Acid Res. 19:1831–1835 (1991).
Piekarowicz, et al., J. Bacteriology, 173:150–155 (1991).
Fomenkov, et al., Nucleic Acids Res. 22:2399–2403 (1994).
Lunnen, et al., Gene, 74:25–32 (1988).
Raleigh and Wilson, Proc. Natl. Acad. Sci, USA, 83:9070–9074 (1986).
Heitman and Model, J. Bact., 196:3243–3250 (1987).
Raleigh, et al., Genetics, 122:279–296 (1989).
Waite–Rees, et al., J. Bacteriology, 173:5207–5219 (1991).
Wilson, Methods in Enzymology, 216:259–279 (1992).
Ochman, et al., Genetics, 120:621 (1988).
Triglia, et al., Nucl. Acids Res. 16:8186 (1988).
Silver and Keerikatte, J. Cell Biochem., (Suppl.) 13E:306, Abstract No. WH239 (1989).
Fuller, Gene, 19:43–54 (1982).
Shimatake and Rosenberg, Nature, 292:128 (1981).
Shine & Dalgarno, Proc. Natl. Acad. Sci. USA, 71:1342–1346 (1974).
Ikemura, J. Mol. Biol., 151:389–409 (1981).
Birnboin and Doly, Nucl. Acids Res., 7:1513 (1973).
Matsudaira, J. Biol. Chem., 262:10035–10038 (1987).
Looney, et al., Gene, 80:193–208 (1989).
Tao, et al., J. Bacteriology, 183:1367–1375 (1991).

*Primary Examiner*—Charles L. Patterson, Jr.
*Attorney, Agent, or Firm*—Gregory D. Williams

[57] ABSTRACT

The present invention relates to the recombinant DNA which encodes the SpeI restriction endonuclease and modification methylase, and the production of SpeI restriction endonuclease from the recombinant DNA.

6 Claims, 3 Drawing Sheets

FIG. 1

The DNA of *Sphaerotilus species* (ATCC #13923) is purified.
↓
A selectable vector, pSspIHincII/SpeI, containing 2 *Spe*I sites is constructed and libraries of *Sphaerotilus species* DNA are made in this vector.
↓
Clones expressing the *Spe*I methylase are identified by the methylase selection method.
↓
The DNA of an *Spe*I methylase clone is sequenced and the location and the orientation of the *Spe*I methylase gene is determined.
↓
DNA 3' to the *Spe*I methylase gene is amplified by inverse PCR techniques and sequenced
↓
The *Spe*I restriction endonuclease protein is purified to near homogeneity.
↓
The N-terminal amino acid sequence of the *Spe*I endonuclease is determined.
↓
The *Spe*I endonuclease gene and control gene are identified
↓
The *Spe*I methylase is expressed by amplifying the *Spe*I methylase gene from *Sphaerotilus species* DNA and ligating the gene into vector pSYX20 to form pSYX20SpeIM9.
↓
The *Spe*I endonuclease is expressed by amplifying the *Spe*I endonuclease gene from *Sphaerotilus species* DNA, ligating the gene into the expression vector pRRS and introducing this construct into an *E. coli* strain premodified by the *Spe*I methylase construct, pSYX20SpeIM9.
↓
The *Spe*I endonuclease clone is grown in a fermenter in L-broth with the appropriate antibiotic selection and induction.
↓
The *Spe*I endonuclease is purified by protein purification techniques.

METHOD FOR CLONING AND PRODUCING THE SPEI RESTRICTION ENDONUCLEASE

BACKGROUND OF THE INVENTION

The present invention relates to the recombinant DNA which encodes the SpeI restriction endonuclease and modification methylase, and the production of SpeI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. More than one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different type II restriction endonucleases, named DraI, DraII and DraIII. These enzymes recognize and cleave the sequences TTTAAA, PuGGNCCPy and CACNNNGTG, respectively. Escherichia coli RY13, on the other hand, synthesizes only one type II restriction enzyme, EcoRI, which recognizes the sequence GAATTC.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178: 717–719, (1980); HhaII: Mann et al., *Gene* 3: 97–112, (1978); PstI: Walder et al., *Proc. Nat Acad. Sci.* 78 1503–1507, (1981), the disclosures of which are hereby incorporated by reference herein). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12: 3659–3676, (1984); PaeR7: Gingeras and Brooks, *Proc. Natl. Acad. Sci. USA* 80: 402–406, (1983); Theriault and Roy, *Gene* 19: 355–359 (1982); PvuII: Blumenthal et al., *J. Bacteriol.* 164: 501–509, (1985), the disclosures of which are hereby incorporated by reference herein).

A third approach which is being used to clone a growing number of systems, involves selection for an active methylase gene (refer to U.S. Pat. No. 5,200,333 and BsuRI: Kiss et al., *Nucl. Acid. Res.* 13: 6403–6421, (1985), the disclosures of which are hereby incorporated by reference herein). Since restriction and modification genes are often closely linked, both genes can often be cloned simultaneously. This selection does not always yield a complete restriction system however, but instead yields only the methylase gene (BspRI: Szomolanyi et al., *Gene* 10: 219–225, (1980); Bcn I: Janulaitis et al, *Gene* 20: 197–204 (1982); Bsu RI: Kiss and Baldauf, *Gene* 21: 111–119, (1983); and Msp I: Walder et al., *J. Biol. Chem.* 258: 1235–1241, (1983), the disclosures of which are hereby incorporated by reference herein).

Another method for cloning methylase and endonuclease genes is based on a colorimetric assay for DNA damage (see, U.S. Pat. No. 5,492,823). When screening for a methylase, the plasmid library is transformed into the host *E.coli* strain such as AP1-200. The expression of a methylase will induce the SOS response in an E.coli strain which is McrA$^+$, McrBC$^+$, or Mrr$^+$. The AP1-200 strain is temperature sensitive for the Mcr and Mrr systems and includes a lac-Z gene fused to the damage inducible dinD locus of *E.coli*. The detection of recombinant plasmids encoding a methylase or endonuclease gene is based on induction at the restictive temperature of the lacZ gene. Transformants encoding methylase genes are detected on LB agar plates containing X-gal as blue colonies. (Piekarowicz, et.al., *Nucleic Acids Res.* 19:1831–1835, (1991) and Piekarowicz, et.al. *J. Bacteriology* 173:150–155 (1991), the disclosures of which are hereby incorporated by reference herein). Likewise, the *E.coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et.al. *Nucleic Acids Res.* 22:2399–2403 (1994), the disclosure of which is hereby incorporated by reference herein).

Sometimes the straight-forward methylase selection method fails to yield a methylase (and/or endonuclease) clone due to various obstacles. See, e.g., Lunnen, et al., *Gene,* 74(1):25–32 (1988), the disclosure of which is hereby incorporated by reference herein. One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease (see, U.S. Pat. No. 5,320,957).

Another obstacle to cloning restriction-modification systems lies in the discovery that some strains of *E.coli* react adversely to cytosine or adenine modification; they possess systems that destroy DNA containing methylated cytosine (Raleigh and Wilson, *Proc. Natl. Acad. Sci., USA* 83:9070–9074, (1986), the disclosure of which are hereby incorporated by reference herein) or methylated adenine (Heitman and Model, *J. Bact.* 196:3243–3250, (1987); Raleigh, Trimarchi, and Revel, *Genetics,* 122:279–296, (1989) Waite-Rees, et al., *J. Bacteriology,* 173:5207–5219 (1991), the disclosures of which are hereby incorporated by reference herein). Cytosine-specific or adenine-specific methylase genes cannot be cloned easily into these strains, either on their own, or together with their corresponding endonuclease genes. To avoid this problem it is necessary to use mutant strains of *E. coli* (McrA$^-$ and McrB$^-$ or Mrr$^-$) in which these systems are defective.

A third potential difficulty is that some restriction endonuclease and methylase genes may not express in *E. coli* due to differences in the transcription machinery of the source organism and *E. coli,* such as differences in promotor and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY

The present invention relates to recombinant DNA encoding the genes for the SpeI restriction endonuclease and modification methylase obtainable from *Sphaerotilus* species as well as related methods for the production of these enzymes from the recombinant DNA. This invention also relates to a transformed host which expresses the restriction endonuclease SpeI, an enzyme which recognizes the DNA sequence 5' ACTAGT3' and cleaves the phosphodiester bond on the 5' side of the C residue of this recognition sequence to produce a 4 base 5' extension. SpeI restriction endonuclease produced according to the present invention is substantially pure and free of the contaminants normally found in restriction endonuclease preparations made by conventional techniques.

The SpeI methylase gene, but not the SpeI endonuclease gene, was obtained generally in accordance with the technique referred to as methylase selection (U.S. Pat. No. 5,200,333, the disclosure of which is hereby incorporated by reference herein). However none of the clones obtained by methylase selection expressed detectable SpeI restriction endonuclease activity. A methylase clone was sequenced and the SpeI methylase gene was identified based on homology to other N6-adenine methylases. The clone contained approximately 3 kb of DNA 5' to the SpeI methylase gene, however the cloned DNA ended very near the 3' end of the methylase gene. Since the methylase clone did not produce any detectable SpeI endonuclease activity, it was speculated that the endonuclease gene was probably located 3' to the methylase gene. DNA contiguous to the 3' end of the SpeI methlase clone was therefore amplified from *Sphaerotilus* species by inverse PCR techniques and sequenced.

To locate and positively identify the SpeI endonuclease gene, the N-terminal amino acid sequence of highly purified SpeI restriction endonuclease protein obtained from *Sphaerotilus* species was determined. This amino acid sequence was compared with the amino acid translation of the DNA sequence of the methylase clones obtained from the methylase selection technique and no match was found. An open reading frame in which the deduced amino acid sequence matched the N-terminal amino acid sequence of the SpeI endonuclease was observed in the DNA sequence 3' of the methylase gene obtained by inverse PCR techniques. The endonuclease open reading frame was orientated convergent with respect to the methylase gene, and a control, or C protein, open reading frame was observed immediately preceeding the endonuclease orf. The SpeI endonuclease gene was then amplified, ligated to an expression vector, and introduced into a host which was premodified with the SpeI methylase carried on a separate compatible vector. A host carrying the endonuclease and methylase genes was then grown, induced and harvested and used to make the SpeI endonuclease.

The preferred method for cloning the SpeI restriction-modification system consists of obtaining methylase positive clones according to methylase selection method, determining the DNA sequence of SpeI methylase positive clones, amplifying the adjacent DNA 3' to the methylase gene by inverse PCR techniques and sequencing this DNA. The SpeI endonuclease protein from *Sphaerotilus* species is purified to near homogeneity and the N-terminal amino acid sequence determined. The SpeI endonuclease gene is identified based on the DNA sequence and amino acid sequence data. The SpeI endonuclease is then expressed by amplifying the complete gene from *Sphaerotilus* species genomic DNA and ligating it into an expression vector such as pRRS (New England Biolabs, Inc., Beverly, Mass.). The construct is introduced into a host which is premodified at SpeI sites by virtue of carrying the SpeI methylase gene expressed on a separate compatible plasmid such as pSYX20 (New England Biolabs, Inc., Beverly, Mass.). The SpeI endonuclease is produced by growing the host containing the SpeI endonuclease and methylase genes, inducing with the appropriate expression condition, harvesting the cells and purifying the SpeI endonuclease.

BRIEF DESCRIPTION OF THE DRAWINGS

FIG. 1 illustrates the preferred method for cloning and producing the SpeI restriction endonuclease.

DETAILED DESCRIPTION OF THE INVENTION

Figure 2:
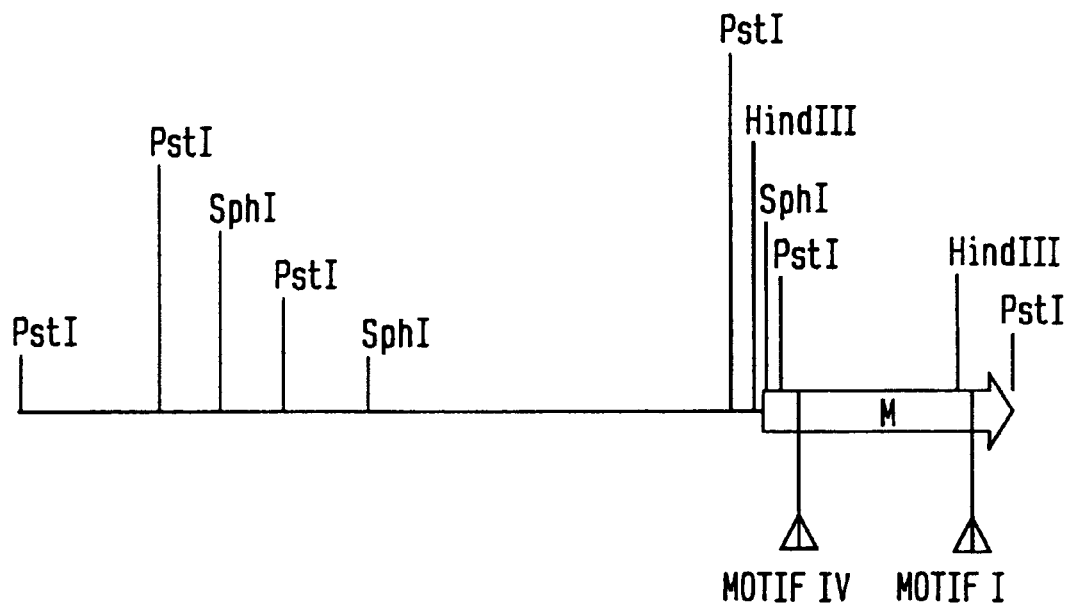
FIG. 2 is a restriction map of the *Sphaerotilus* species DNA contained in the methylase clone pSpeIM1. This clone pSpeIM1 is obtained by methylase selection and contains a functional SpeI methylase. The location and orientation of the SpeI methylase is shown.

The present invention relates to recombinant DNA which encodes the SpeI restriction endonuclease and methylase, as well as to the enzymes produced from such a recombinant DNA.

The cloning of the SpeI restriction endonuclease gene from *Sphaerotilus* species proved to be challenging. Methylase clones were obtained by the methylase selection procedure but these failed to yield the endonuclease gene. In order to perform methylase selection, a vector containing two SpeI sites was created by inserting a 12 bp oligomer containing an SpeI site into the SspI and HincII sites of pUC19 to form the vector pSspIHincII/SpeI. 'Shotgun' libraries of *Sphaerotilus* species DNA partially cleaved by PstI were constructed in the pSspIHincII/SpeI vector. Purified DNA of the shotgun plasmid library was subjected to SpeI endonuclease digestion and transformed back into *E. coli*. Clones containing a functional SpeI methylase gene are protected from SpeI digestion by virtue of methylase modification. This allows selection of clones carrying the methylase gene, as such clones survive the endonuclease challenge intact. DNA from the survival clones was subsequently purified and the presence of an active methylase gene was confirmed by protection from digestion by SpeI endonuclease. Two clones containing identical 4 kb inserts were found to be protected from SpeI digestion. In order to determine the location and orientation of the methylase gene, one of these clones, designated pSpeIM1, was subjected to DNA sequencing. Deduced amino acid translation of the DNA sequence revealed an open reading frame containing two amino acid sequence motifs consistent with an $m^6A_\beta$-type adenine methylase (Wilson, *methods in Enzymology*, 216:259–279 (1992), the disclosure of which is hereby incorporated by reference herein).

The methylase clones obtained from methylase selection were tested for SpeI endonuclease activity, but no detectable endonuclease activity was observed. Either the SpeI endonuclease gene was present on the methylase clones but failed to express in *E. coli* at a detectable level or the methylase clones did not contain the SpeI endonulcease gene.

In order to locate and positively identify the SpeI endonuclease gene, the N-terminal amino acid squence of the SpeI restriction endonuclease was determined, as was DNA sequence information for *Sphaerotilus* species DNA immediately 3' to the methylase gene. To obtain the N-terminal amino acid sequence of the Spe I restriction endonuclease protein, a protein purification scheme was developed to purify the SpeI protein to near homogeneity. The first 28 amino acid residues were delineated by sequential degradation of the purifed protein on an automated sequencer. To obtain DNA sequence information regarding the *Sphaerotilus* species DNA 3' to the methylase gene this DNA was amplified by inverse PCR techniques (Ochman, et al., *Genetics*, 120:621 (1988), Triglia, et al., *Nucl. Acids Res.*, 16:8186 (1988) and Silver and Keerikatte, *J. Cell. Biochem.*, (Suppl.) 13E:306, Abstract No. WH239 (1989), the disclosures of which are hereby incorporated by reference herein) and the amplified product was sequenced. The SpeI endonuclease gene was then positively identified by comparing the 6 frame amino acid translation of this DNA sequence and the N-terminal amino acid sequence of the SpeI endonuclease protein.

Figure 3:
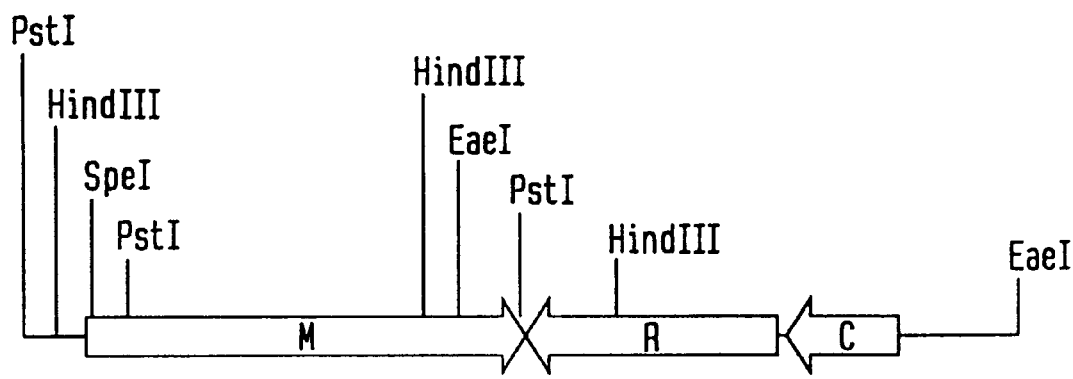
FIG. 3 shows the relative locations and orientations of the SpeI methylase gene, the SpeI endonuclease gene and the SpeI control gene.

It was also found that an open reading frame (ORF) of 246 bp adjacent to the 5' end of the SpeI endonuclease gene exhibits extensive homology to the control (C) genes of some other restriction-modification systems found to date. This ORF is thus believed to be the SpeI control gene. FIG. 3 shows the locations and orientations of the SpeI methylase gene, the SpeI endonuclease gene and the putativeSpeI control gene.

To clone and express the SpeI endonuclease a two-step cloning strategy was attempted. In order to stabilize bacterial hosts containing the SpeI endonuclease gene, the DNA of the hosts was first methylated at SpeI sites by introducing the SpeI methylase gene on a separate vector compatible with the expression vector carrying the endonuclease gene. To this end, oligonucleotide primers were designed and synthesized to amplify the SpeI methylase gene and facilitate its expression in the pSYX20 vector (New England Biolabs, Inc., Beverly, Mass.). The methylase gene was amplified from *Sphaerotilus* species DNA, the amplified product was cleaved with the appropriate restriction enzymes and ligated into the vector pSYX20, previously cleaved with the same restriction endonucleases, and transformed into *E. coli* ER2427 (New England Biolabs, Inc., Beverly, Mass.) host cells. Individual transformants were picked and analyzed for protection from SpeI endonuclease cleavage.

To clone the endonuclease without the control gene, synthetic DNA primers were designed to precisely amplify the SpeI endonuclease gene. The forward primer had the following elements: an NsiI cloning site, a stop codon in frame with the lacZ gene to terminate translation of the lacZ protein, a strongly recognized ribosome binding site, seven nucleotide spacer between the rbs and the ATG start codon of the SpeI endonulcease gene and sequence complementary to *Sphaerotilus* species DNA for hybridization. The 3' (reverse) primer was designed to hybridize just at the 3' end of the endonuclease gene, to minimize overlap with the methylase clone. A restriction site for BamHI was introduced in this primer to facilitate cloning. The endonuclease gene was amplified from genomic *Sphaerotilus* species DNA. The amplified DNA was cleaved by NsiI and BamHI and ligated into the expression vector PRRS, which had been previously cleaved by PstI and BamHI and gel purified. The ligation reaction was transformed into *E. coli* ER2427 competent cells carrying the SpeI methylase gene in pSYX20. Vectors containing inserts of the desired size were identified by miniprep procedures. These clones were grown to mid-log phase and induced with IPTG. The cells were then harvested by centrifugation, resuspended in sonication buffer and lysed by sonication. The extracts were assayed for SpeI endonuclease activity. One SpeI expressing host, pSpeIR7 was propagated and used to produce SpeI restriction endonuclease. SpeI endonuclease can be purified by a protein purification scheme described herein below.

The method described herein by which the SpeI restriction endonuclease and methylase genes are preferably cloned and expressed is illustrated in FIG. 1 and includes the following steps:

1. Sphaerotilus species (ATCC #13923) is grown in flasks containing CGYA media (ATCC #1103), the cells are lysed and the genomic DNA purified.

2. Random libraries of *Sphaerotilus* species DNA are constructed. A vector containing two SpeI sites, pSspIHincII/SpeI is constructed by introducing a DNA oligomer containing an SpeI site into the HincII and SspI sites of pUC19. *Sphaerotilus* species DNA is partially digested with PstI and ligated into the vector pSspHincII/SpeI. The ligated DNA is transformed into *E. coli,* the transformants are pooled and the populations of plasmids are purified to form libraries.

3. The methylation selection method is used to select for SpeI methylase clones. The PstI library is digested with SpeI endonuclease. The SpeI restricted plasmids are transformed back into *E. coli* to recover uncut clones. A number of individual transformants of plasmids surviving SpeI digestion are grown and mini-preparations are made of their plasmids. The plasmids are analyzed for resistance to SpeI endonuclease digestion. Two identical clones are found that are protected from SpeI cleavage. These both contain a 4 kb insert. The methylase positive clones are assayed for SpeI restriction endonuclease activity, but no activity can be detected.

4. Sequencing the SpeI methylase clones: A portion of the DNA of the 4 kb insert of clone pSpeIM1 is sequenced. An open reading frame starting with a methionine with amino acid sequences homologous to the conserved regions (motifs I and IV) of an $m^6A_\beta$-type methylase is observed and identified as the SpeI methylase. The methylase reading frame was open continuous on the 3' end into the vector. (It was subsequently found that the methylase clones recovered were missing the last four amino acids codons of the SpeI methylase gene.)

5. DNA adjacent and 3' to the methylase gene is amplified by inverse PCR techniques using primers that hybridize within the SpeI methylase gene. The DNA sequence of the inverse PCR products is determined.

6. The SpeI restriction endonuclease protein is purified to near homogeneity from *Sphaerotilus* species by a combination of protein purification techniques developed at New England Biolabs (see Example, step 6). The endonuclease so purified is nearly homogeneous on SDS polyacrylamide gel electrophoresis and has an apparent molecular weight of approximately 20 kilodaltons.

7. The amino terminal amino acid sequence of the endonuclease is obtained using an Applied BioSystems Division, Perkin-Elmer Corporation (Foster City, Calif.) 470A Protein Sequencer (Waite-Rees, P. A., Keating, C. J., Moran, L. S., Slatko, B. E., Hornstra, L. J. and Benner, J. S., J. Bacteriol. 173:5207–5219, 1991), the disclosure of which is hereby incorporated by reference herein).

8. The SpeI endonuclease gene is identified by comparing the amino acid translation of DNA sequences adjacent to the SpeI methylase gene with the amino acid sequence data obtained from N-terminal amino acid sequencing of the SpeI endonuclease. The SpeI methylase gene and the endonuclease gene are orientated convergent with respect to each other, with their 3' ends overlaping by 14 amino acid residues. An open reading frame coding for a peptide of 82 amino acids is located 5' to and oriented in the same direction as the endonuclease gene. The amino acid sequence of this orf is highly homologous to control genes found in some other restriction-modification systems, and is thus identified as the SpeI control gene.

9. Overexpressing the SpeI endonuclease gene:

A. General considerations:

There are a number of ways in which the restriction gene can be overexpressed. The DNA sequence and detailed mapping information help determine the best approach for overexpression of the restriction endonuclease gene.

One approach for overexpression comprises designing primers that hybridize directly at the N-terminus of the restriction endonuclease gene and somewhere downstream (3') of the gene in order to use the polymerase-chain reaction to amplify the entire endonuclease gene. The resulting DNA fragment can be inserted into an expression vector such as pAII17 or pRRS directly downstream of an inducible promoter (T7 or PlacUV5).

Alternatively, overexpression can be accomplished by inserting a promoter recognized strongly by *E. coli,* such as Ptac on pAGR3 (New England Biolabs, Inc.; Beverly, Mass.) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the Ptac promoter. Other regulated promoters which can be used are PlacUV5 (Fuller, *Gene* 19:43–54 (1982), the disclosure of which is hereby incorporated by reference herein), and IPL (Shimatake and Rosenberg, *Nature* 254:128 (1981), the disclosure of which is hereby incorporated by reference herein) on pUC19 and pBR322 derivatives. In addition, a strong ribosome binding site (Shine & Dalgarno, *Proc. Natl. Acad. Sci. USA* 71: 342–1346 (1974), the disclosure of which is hereby incorporated by reference herein) can be placed in front of the gene to increase expression.

To obtain a stable clone which overexpresses the restriction endonuclease, the host is generally pre-protected from restriction endonuclease digestion. In the present invention this is accomplished by cloning the SpeI methylase on a separate plasmid. The plasmid used must be compatible with the expression vector. The methylase also must be produced at a level which will protect the host's genome from digestion by the overexpressed restriction endonuclease gene.

The DNA sequence of the gene can be altered by site-directed mutagenesis or by resynthesizing the gene itself to use codons that are more efficiently utilized in *E. coli* (Ikemura, *J. Mol. Biol.* 151:389–409 (1981), the disclosure of which is hereby incorporated by reference herein).

B. Cloning the SpeI methylase in a compatible vector:

DNA primers are designed and synthesized to amplify the SpeI methylase gene. The forward primer has the following elements: A BamHI site to facilitate cloning, a stop codon to end translation of the tetracycline gene, a consensus *E. coli* ribosome binding site, 7 nucleotide spacer between the rbs and the ATG start codon of the SpeI methylase and 19 nucleotides matching the SpeI methylase gene DNA sequence for hybridization. The reverse primer has a SalI site to facilitate cloning and 19 nucleotides matching the SpeI methylase gene DNA sequence at the 3' end of the SpeI methylase gene. The methylase gene is amplified from the genomic DNA using these primers and cloned into the vector pSYX20 (New England Biolabs, Inc.; Beverly, Mass.). Individual clones are miniprepped and those containing the desired size insert are checked for methylase expression by introducing the vector Litmus 38 (New England Biolabs, Inc.; Beverly, Mass.), which contains one SpeI site, into *E. coli* cells containing pSYX20 methylase constructs, performing minipreps and digesting with SpeI. All clones tested express methylase activity well enough to fully protect plasmid Litmus 38 from digestion by SpeI. Competent cells are made from a single clone, designated pSYX20SpeIM9, for subsequent SpeI endonuclease expression.

C. Expression of SpeI endonuclease:

DNA primers are designed and synthesized to amplify the SpeI endonuclease gene. The forward primer has the following elements: an NsiI cloning site, stop codon in frame with the lacZ gene, *E. coli* consensus strong ribosome binding site, 7 nucleotide spacer sequence between the ribosome binding site and the ATG start codon of the SpeI endonuclease and 21 nucleotides matching the SpeI endonuclease DNA sequence for hybridization. The reverse (3') primer has a BamHI site to facilitate cloning and 20 nucleotides matching *Sphaerotilus* species DNA at the 3' end of the endonuclease gene for hybridization. The endonuclease gene is amplified from the genomic DNA using these primers. The amplified DNA is cleaved by NsiI and BamHI and ligated into the expression vector pRRS, which has been previously cleaved by PstI and BamHI endonucleases and gel purified. The ligation reaction is transformed into *E. coli* ER2427 competent cells containing pSX20SpeIM9. Vectors containing inserts of the desired size are identified by miniprep procedures. Several of these clones are grown to mid-log phase and induced with 0.5 mM IPTG for 16 hours. The cells are then harvested by centrifugation, resuspended in sonication buffer and lysed by sonication and the extract assayed for SpeI endonuclease activity. One such SpeI expressing host, designated pSpeIR7, is propagated and used to produce SpeI restriction endonuclease.

10. Production: The SpeI endonuclease may be produced from host cells carrying the overexpressed SpeI restriction endonuclease gene and SpeI methylase gene by propagation in a fermenter in a rich medium with the appropriate antibiotic selection and induction. The cells are thereafter harvested by centrifugation and disrupted by sonication to produce a crude cell extract containing SpeI restriction endonuclease activity.

11. Purification: The crude cell extract containing the SpeI endonuclease is purified by a combination of protein purification techniques, such as affinity-chromatography or ion-exchange chromatography.

Although the above-outlined steps represent the preferred mode for practicing the present invention, it will be apparent to those skilled in the art that the above described approach can vary in accordance with techniques known in the art.

The following Example is given to illustrate embodiments of the present invention as it is presently preferred to practice. It will be understood that this Example is illustrative, and that the invention is not to be considered as restricted thereto except as indicated in the appended claims.

EXAMPLE

Cloning of the SpeI Modification Methylase and SpeI Restriction Endonuclease Genes 1. DNA purification: To prepare the genomic DNA of *Sphaerotilus* species (ATCC #13923), 28 grams of cell paste were resuspended by grinding the sheath from the cells with mortar and pestle in 5 ml of 25% sucrose, 0.05M Tris-HCl pH 8.0. 45 ml of 25% sucrose, 0.05 M Tris-HCl, pH 8.0 was added to the ground cells followed by 25 ml of 0.25 M EDTA, pH 8.0. 24 ml of lysozyme solution (10 mg/ml lysozyme in 0.25 M Tris-HCl, pH 8.0) was added and the solution was incubated at 37° C. for 2 hours. 48 ml of Lytic mix (1% Triton-X100, 50 mM Tris, 62 mM EDTA, pH 8.0) was then added and the solution was again incubated at 37° C. for 30 minutes. The solution was extracted with one volume of equilibrated phenol:chloroform (50:50, v/v) and the aqueous phase was recovered and extracted with one volume of chloroform two times. The aqueous solution was then dialysed against four changes of 2 L of 10 mM Tris, 1 mM EDTA, pH 8.0. The dialysed solution was digested with RNase (100 ug/ml) at 37° C. for 1 hour. The DNA was precipitated by the addition of 1/10th volume 5 M NaCl and 0.55 volume of 2-propanol and spooled on a glass rod. The DNA was air dried and dissolved in 15 ml TE (10 mM Tris, 1 mM EDTA, pH 8.0) to a concentration of approximately 160 ug/ml and stored at 4° C.

2. Contruction of random libraries of *Sphaerotilus* species DNA in a selectable vector.

A. Construction of a selectable vector pSspIHincII/SpeI:

A 12 nucleotide DNA oligomer was synthesized containing an SpeI site as follows. The 5° C. residue was phosphorylated to facilitate ligation.

SpeI linker: 5'-pCCAACTAGTTGG-3' (SEQ ID NO:1)

The linkers were inserted into two sites in the vector pUC19; SspI (2501) and HincII (429).

(1): Constructing vector with 1 SpeI site: 6 $\mu$g of pUC19 DNA were digested with 25 units of SspI in a final volume of 50 $\mu$l in 1× NEB#2 buffer (10 mM Tris-HCl, 10 mM MgCl$_2$, 50 mM NaCl, 1 mM DTT, pH 7.9 at 25° C.) for 2 hours at 37° C. 10 units of calf intestinal alkaline phosphatase, or CIP, (NEB #290) was added and the reaction was incubated for 1 hour. The enzymes were heat-inactivated at 78° C. for 20 minutes. 240 ng (2 $\mu$l) of SspI digested, dephosphorylated vector was ligated to 4.5 $\mu$g of SpeI self-annealled linker in a final volume of 30 $\mu$l in 1× ligase buffer (50 mM Tris-HCl, pH 7.5, 10 mM MgCl$_2$, 10 mM DTT, 1 mM ATP) with 1200 units T4 DNA Ligase (New England Biolabs, Inc.; Beverly, Mass.). The reaction was incubated overnight at 16° C. and then was transformed in *E. coli* strain RRI (ATCC 31343). The transformed cells were plated onto Luria Broth (L-Broth) agar plates supplemented with 100 $\mu$g/ml ampicillin and incubated at 37° C. overnight. Clones of the desired construct were identified by performing minipreps, digesting the purified DNA with SpeI and analyzing by agarose gel electrophoresis. One clone containing the desired construct was designated pSspI/SpeI and used in the following steps.

Analysis of plasmid clones: Individual transformants were inoculated into 1.8 ml cultures of L-broth containing 100 ug/ml ampicillin and the plasmids that they carried were prepared by the following miniprep plasmid purification procedure, adapted from the method of Birnboin and Doly (*Nucleic Acids Res.* 7:1513 (1973), the disclosure of which is hereby incorporated by the reference herein) as described below. Plasmids were assayed for the presence of linker by digesting with SpeI.

Miniprep Procedure: 1.5 ml of each culture was centrifuged at 8000 rpm for 2 minutes; the supernatant was discarded and the cell pellet was resuspended in 200 $\mu$l of 25 mM Tris, 10 mM EDTA, 50 mM glucose, pH 8.0. 400 $\mu$l of a freshly prepared solution of 0.2 M NaOH, 1% SDS was added to each tube and the tubes were shaken to lyse the cells. Once the solutions had cleared, 300 μl of 3 M NaAcetate pH 4.8 was added to each and gently mixed by shaking. The precipitates that formed were spun down at 14,000 rpm at 4° C. for 3 minutes. Each supernatant was poured into a centrifuge tube containing 700 μl of isopropanol and mixed. The tubes were spun at 14,000 rpm at 4° C. for 5 minutes to pellet the precipitated nucleic acids. The supernatants were discarded and the pellets were air-dried at room temperature for 15 minutes. Once dried, the pellets were dissolved in 250 μl of 10 mM Tris pH 8.0, 1 mM EDTA, containing 50 μg/ml RNase and incubated for 1 hour at 37° C. to digest the RNA. The DNA was precipitated by the addition of 25 μl of 5 M NaCl followed by 175 μl of 2-propanol. The DNA was collected by centrifugation for 5 minutes at 4° C., the supernatants were discarded, the pellets were dried and then redissolved in 50 μl of 10 mM Tris, 1 mM EDTA pH 8.0 (1× TE). The plasmid minipreps were subsequently analyzed by digestion with various restriction enzymes.

(2): Constructing a vector with 2 SpeI sites: 0.5 μg of pSsp/SpeI was digested with 20 units of HincII in a final volume of 50 μl in 1× NEB#4 buffer (20 mM Tris-acetate, 10 mM magnesium acetate, 50 mM potassium acetate, 1 mM DTT, pH 7.9 at 25° C.) for 2 hours at 37° C., followed by dephosphorylation with 5 units CIP as above. The enzymes were heat-inactivated at 78° C. for 20 minutes. 40 ng of HincII digested, dephosphorylated DNA was ligated to 4.5 μg of SpeI linker in a final volume of 30 ul in 1× ligase buffer with 1200 units T4 DNA Ligase. The reaction was incubated overnight at 16° C. and was then transformed in E. coil strain RRI. The transformed cells were plated onto LB agar plates supplemented with 100 μg/ml ampicillin and incubated at 37° C. overnight. Clones of the desired construct were identified by performing minipreps, digesting the purified DNA with SpeI and analyzing the digestion products by agarose gel electrophoresis. One clone having the desired construct of two SpeI restriction sites was designated pSspIHincII/SpeI and used as a selectable vector for SpeI genomic libraries construction.

B. Constructing SpeI genomic libraries:

Approximately 15 μg of *Sphaerotilus* species genomic DNA was partially digested with PstI in a final volume of 100 μl in NEB#3 buffer (50 mM Tris-HCl, 10 mM MgCl₂, 100 mM NaCl, 1 mM DTT, pH 7.9 at 25° C.) supplemented with 0.1 mg/ml BSA and incubated at 37° C. for 1 hour. The partial digestion was carried out by serial dilution of the PstI restriction endonuclease from 2.7 units/ug DNA to 0.016 units/ug. The reactions were subsequently terminated by heating at 78° C. for 20 minutes. 5 ug of digested SpeI genomic DNA from each of the PstI partial digestion reaction was ligated to 1 ug of the vector pSspIHincII/SpeI (previously cleaved by PstI, dephosphorylated with calf intestinal alkaline phosphatase and gel purified) in a final volume of 50 ul in 1× NEB ligase buffer with 1000 units of T4 DNA ligase. The reactions were left at room temperature for 16 hours. 10 ul of the each ligation reaction mixture was then transformed into *E. coli* RRI cells and plated onto L-Broth agar plates supplemented with 100 ug/ml ampicillin. The plates were incubated at 37° C. overnight. A total of 14,500 individual transformants were obtained and pooled together by scraping into 14 ml of 10 mM Tris, 10 mM MgCl₂, pH 7.5 and mixed well. 2 ml of this pool was used to innoculate 500 ml of L-broth supplemented with 100 ug/ml ampicillin and the culture was grown with shaking at 37° C. overnight. The cells were harvested by centrifugation at 4 K rpm for 5 minutes. The cell pellet was resuspended in 10 ml of 25% sucrose, 50 mM Tris-HCl, pH 8.0 followed by the addition of 5 ml of 250 mM EDTA, pH 8.0 and 3 ml of 10 mg/ml lysozyme in 250 mM Tris-HCl, pH8.0. This suspension was left on ice for one hour and then 12 ml of Lytic mix (50 mM Tris-HCl, 62.5 mM EDTA, 1% Triton X-100, pH 8.0) were added and this mixture was left on ice for 10 minutes. The lysed mixture was centrifuged at 17 K rpm at 4° C. for 45 minutes. 22 g of the supernatant was mixed with 20 g of CsCl and 1 ml of 5 mg/ml ethidium bromide in 10 mM Tris-HCl, 1 mM EDTA, 100 mM NaCl, pH 8.0. The solution was transferred to two ⅝ in.×3 in. centrifuge tubes and spun in a Beckman Ti70 rotor for 30 hours at 50 K rpm, 17° C. The plasmids were isolated by illuminating the bands with ultraviolet light, and collecting them with a syringe and needle. The samples from the two tubes were pooled and the ethidium bromide was removed by extracting 5 times with buffer-saturated, cold N-butanol. The aqueous solution was placed in 10 mm dialysis tubing and dialyzed 4 times against 2 L TE (10 mM Tris-HCl, 1 mM EDTA, pH 8.0). The dialyzed solution was then precipitated with 2 volumes of cold 2-propanol and ¹/₁₀th volume of 5M NaCl and centrifuged at 15 K rpm for 15 minutes. The pellet was resuspended in 1 ml TE at a final concentration of 1.4 mg/ml.

3. SpeI methylase selection: 2.4 ug of plasmid library was digested with 12 units of Spe I in 1× NEB#1 buffer (10 mM Bis Tris Propane-HCl, 10 mM MgCl₂, 1 mM DTT, pH 7.0 at 25° C.) supplemented with 0.1 mg/ml BSA in a final volume of 50 ul and incubated for 2 hours at 37° C. The sample was extracted with phenol:chloroform (50:50, v/v) and the DNA was precipitated with ¹/₁₀th volume of 5M NaCl and two volumes of 2-propanol. 10 units of CIP (calf intestinal alkaline phosphatase, NEB) were added and the reaction was incubated at 37° C. for 30 minutes followed by 10 additional units of CIP and the reactions were allowed to proceed for 30 more minutes. This reaction was extracted with one volume of equilibrated phenol:chloroform (50:50, v/v) and DNA was precipated with ¹/₁₀th volume 5 M NaCl and 2 volumes of 2-propanol. The DNA pellet was then resuspended in 10 ul TE (10 mM Tris-HCl, 1 mM EDTA, ph7.5), transformed into *E. coli* RRI competent cells and plated on L-broth plates containing 100 ug/ml ampicillin. The plates were incubated at 37° C. overnight. A total of 18 transformants were analyzed as follows: Plasmid from each colony was isolated by miniprep procedures and digested with SpeI endonuclease. 2 clones were found to be fully protected from SpeI digestion. Futher restriction analysis showed these clones were identical and contained a 4 kb insert. One such methylase containing clone was designated as pSpeIM1.

4: DNA Sequencing: DNA sequencing of the 4 kb insert of pSpeIM1 was performed using the Circumvent DNA sequencing kit (New England Biolabs, Inc.; Beverly, Mass.) according to the manufacturer's instructions. To facilitate sequencing, a PvuII/XbaI subclone was made in vector pUC19 that was also resistant to SpeI endonuclease activity. This subclone construct was designated as pSpeIM2. A series of exonuclease deletions was performed using the Exo-Size™ deletion kit (New England Biolabs, Inc.; Beverly, Mass.) on plasmids pSpeIM1 and pSpeIM2 according to the manufacturer's instruction. Miniprep DNA preparations of the clone pSpeIM1, pSpeIM2 and various exonuclease deleted subclones were used as templates and the M13/pUC primers #1233 and #1224 (New England Biolabs, Inc.; Beverly, Mass.) were used as primers for sequencing. Once DNA sequence information was obtained, the six frame amino acid sequences translated from the DNA sequence were compared with the conserved amino acid motifs of known methylases and motifs I and IV of the m6Aβ-type class of methylase were identified. The DNA sequence of motif I was found to be 5'-CACTGCAC CGTAAAGCACTTCCGTTGATGCT-TAAGCTTGTGGGGATGATGGTTC CGCCTTTTG-CAAACAACATCGTACTTGAC-CCGTTTGCTGGTTCGGGTA CCACGCTTGTGGCCGCAAAGCAGCTCG-GTCTCACTTATCTTGGTATCG AG-3' (SED ID NO:2), which translates into the amino acid sequence: HCTVK-PLPLMLKLVGMMVPPFANNIVLDPFAGSGTT LVAAKQLGLTYLGIE (SEQ ID NO:3), where the amino acids in bold match the conserved or nearly conserved residues. The DNA sequence of motif IV was found to be 5'-GGAGACTGCCG CGAACTACTGGCGAAAATCCCT-GCAGCATCTATCGCGGCATGCATT ACAGACCCACCCTAC-3' (SEQ ID NO:4) which translates into the amino acid sequence: GDCRELLAKIPAA-SIAACITDPPY (SEQ ID NO:5). The methylase reading frame was open continuous into the vector in the clone pSpeIM1. The stop codon of the SpeI methylase was subsequently found to be located four amino acid residues beyond the end of the pSpeIM1 clone when *Sphaerotilus* species DNA 3' to the methylase was amplified using inverse PCR methods as described below.

5. Cloning DNA 3' to the SpeI methylase gene:

Template preparation for inverse PCR amplification: 1 ug of *Sphaerotilus* species DNA was digested with 10 units of HindIII restriction endonuclease in 1× NEBuffer #2 in a 50 ul reaction volume for 1 hour at 37° C. The HindIII enzyme was heat inactivated by incubating at 75° C. for 20 minutes. The HindIII digested DNA was circularized by adding 50 ul 10× T4 DNA ligase buffer and 400 ul dH₂O, followed by 5 ul (2000 NEB units) T4 DNA ligase (NEB #202) and incubating at 16° C. for 16 hours. A portion of this circularization ligation reaction was then used as the template for subsequent inverse PCR reactions. Circularized EaeI digested *Sphaerotilus* species DNA was prepared in the same manner.

Primers SpeI-IP1 and SpeI-IP2 of sequences shown below were synthesized. These primers hybridize within the SpeI methylase gene and are oriented in the opposite direction relative to each other.

Primer SpeI-IP1 5'-GTTGGATCCGAGCAGTCTCACCG-3' (SEQ ID NO:6)

Primer SpeI-IP2 5'-GTTCTGCAGCTTTGTCAATGCCGAG-3' (SEQ ID NO:7)

In the reaction that was successful in amplifying the product, a reaction mix was made by combining:

10 ul of 10× Vent™ reaction buffer 6 ul of 4 mM dNTP solution 5 ul of primer SpeI-IP1 at 10 uM concentration 5 ul of primer SpeI-IP2 at 10 uM concentration 4 ul of 100 mM MgSO₄ (6 mM Mg⁺⁺ final concentration)

12.5 ul of circularized DNA template (aproximately 25 ng)

58 ul dH₂O 2 ul (4 units) of Vent™ Exo⁻ polymerase NEB#257

The PCR amplification conditions were: 95° C. for 3 minutes for one cycle, followed by 4 cycles of 95° C. for 20 seconds, 52° C. for 30 seconds and 72° C. for 1.5 minutes, followed by 20 cycles of 95° C. for 20 seconds, 62° C. for 30 seconds and 72° C. for 1.5 minutes. 10 ul of the PCR reaction was analyzed by electrophoresis on a 0.8% agarose gel.

A 400 bp product was observed in the HindIII circular template PCR reaction, and a 1.2 kb product was observed in the EaeI circular template PCR reaction. These two products were gel purified and resuspended in 25 ul 1× TE. These PCR products were then sequenced using an ABI 373 automated sequencing system according to the manufacturer's instructions, using the PCR primers above as the sequencing primers. Two new sequencing primers complementary to newly read sequence were then synthesized, as below, and used to complete the sequencing of the EaeI 1.2 kb PCR product.

Primer SpeI-S1 5'-GAACTATCAAGAGTACTGGCTC-3' (SEQ ID NO:8)

Primer SpeI-S2 5'-GTTGGATCCTCTGCTCGAGCGAGGGGTG-3' (SEQ ID NO:9)

6. Purification of the SpeI restriction endonuclease from *Sphaerotilus* species to near homogeneity:

*Sphaerotilus* species (ATCC#13923) cells were propagated in CGYA media (ATCC #1103) at 30° C. The cells were harvested by centrifugation after 20 hours growth and stored at −70° C. until used. All of the following procedures were performed on ice or at 4° C. 35 g of cell pellet (wet weight) was resuspended in 120 ml of buffer A.1 (20 mM Tris-HCl, 1 mM Dithiothreito (DTT), 0.1 mM EDTA, 0.1 M NaCl, pH 7.5) and broken by sonication. The extract was centrifuged at 15,000 rpm for 10 minutes at 4° C. The supernatant was loaded onto a 25 ml heparin-sepharose column equilibrated with buffer A.1. The column was washed with 60 ml of buffer A.1, followed by a 250 ml linear gradient from 0.1 M NaCl to 1 M NaCl in buffer A (20 mM Tris-HCl, 1 mM Dithiothreitol (DTT), 0.1 mM EDTA, pH 7.5). 5 ml fraction were collected. Fractions were assayed for SpeI restriction activity with T7 DNA and the peak of restriction enzyme activity was found to elute from the column between 0.38 to 0.46 M NaCl and was pooled. The amount of SpeI endonuclease was estimated to be 250,000 units. This heparin-sepharose pool was diluted with 2 volumes of buffer A and applied to a 3 ml heparin-TSK FPLC column (TosoHaas; Philadelphia, Pa.) equilibrated in buffer A.1, followed by a 40 ml linear gradient of 0.1 M NaCl to 0.6 M NaCl in buffer A. 1 ml fractions were collected. Fractions were assayed for SpeI activity with T7 DNA. The peak of restriction enzyme activity eluted between 0.26 and 0.32 M NaCl and 7 fractions were pooled. This heparin-TSK pool contained approximately 210,000 units SpeI activity. The pool was diluted with 3.5 volumes of buffer A and loaded onto a 1 ml Mono Q FPLC column (Pharmacia: Piscataway, N.J.) equilibrated with Buffer A containing 60 mM NaCl (A.06), washed with 6 ml of buffer A.06 and then a 40 ml linear gradient from 0.1 M NaCl to 0.6 M NaCl in Buffer A was formed. 1 ml fractions were collected. Fractions were assayed for SpeI activity with T7 DNA. The SpeI activity eluted with the wash and was pooled. This Mono Q pool was then loaded onto a 1 ml Mono S FPLC column (Pharmacia: Piscataway, N.J.) equilibrated with buffer A.06, washed with 6 ml of buffer A.06 followed by a 40 ml linear gradient from 0.1 M NaCl to 0.6 M NaCl in buffer A. 1 ml fractions were collected. Fractions were assayed for SpeI activity with T7 DNA. All of the enzyme activity eluted with the wash and was pooled. This Mono S pool was adjusted to 0.1 M final NaCl concentration and loaded onto a 3 ml heparin-TSK FPLC column (TosoHaas; Philadelphia, Pa.) equilibrated in buffer A.1 followed by a 40 ml linear gradient of 0.1 M NaCl to 0.6 M NaCl in buffer A. 1 ml fractions were collected. Fractions were assayed for SpeI activity with T7 DNA. The peak of the enzyme activity eluted at 0.35 M NaCl. Approximately 20,000 units of SpeI activity were purified to near homogeneity. 16 μl of the peak fraction was loaded onto an SDS-PAGE protein gel and subjected to electrophoresis. The gel was stained with Coomassie blue R-250 and a prominent band at approximately 20 kD corresponding to the SpeI restriction endonuclease activity was observed.

7. Amino Terminal SpeI protein sequence:

The SpeI restriction endonuclease, prepared as described in section 6 above, was subjected to electrophoresis and electroblotted according to the procedure of Matsudaira (Matsudaira, P., J. Biol. Chem. 262:10035–10038, 1987), with modifications as previously described (Looney, M. C., Moran, L. S., Jack, W. E., Feehery, G. R., Benner, J. S., Slatko, B. E., & Wilson G. G., Gene 80:193–208, 1989). The membrane was stained with Coomassie blue R-250 and the protein band of approximately 20 kd was excised and subjected to sequential degradation on an Applied BioSystems Division, Perkin-Elmer Corporation (Foster City, Calif.) Model 407A gas phase protein sequencer (Waite-Rees, P.A., Keating, C. J., Moran, L. S., Slatko, B. E., Hornstra, L. J. and Benner, J. S., J. Bacteriol. 173:5207–5219, 1991). The first 28 residues of the 20 kd protein corresponded to (Met)-Ser-lle-Asp-Pro-Asn-Lys-Leu-Asn-Ser-Ala-Leu-Asp-Ala-lle-Leu-Glu-Gly-Tyr-Xxx-Gly-Glu-Phe-Ser-Asn-Lys-Val-Tyr (SEQ ID NO:10). This data was used to compare with amino acid sequence deduced from the DNA sequence 3' to the methylase gene to identify the endonuclease gene.

8. Identifying the SpeI Restriction-Modification system:

The SpeI endonuclease gene is identified by comparing the amino acid translation of DNA sequences adjacent to the SpeI methylase gene with the amino acid sequence data obtained from N-terminal amino acid sequencing of the SpeI endonuclease. An open reading frame convergent with the SpeI methylase gene and overlaping the methylase gene by 14 amino acid residues at their 3' ends was found in which the first 28 amino acids coded for in the DNA sequence match the amino acid sequence determined from the SpeI endonuclease protein. The ambiguous residue X at position 20 of the amino acid sequencing results was found from the DNA sequence to be an arginine. In addition, an open reading frame coding for a peptide of 82 amino acids is located immediately 5' to and oriented in the same direction as the endonuclease gene. The amino acid sequence of this orf is highly homologous to control genes found in some other restriction-modification systems (Tao, et al., J. of Bacteriology, 183:1367–1375 (1991), the disclosure of which is hereby incorporated by reference herein), and is thus identified as the SpeI control gene.

9. Overexpressing the SpeI endonuclease:

A. Cloning the SpeI methylase on a compatable vector:

The SpeI methylase gene was expressed by inserting the gene into the tetracyline gene of pSYX20 to take advantage of the tet gene's transcription system. To accomplish this, two oligonucleotide primers were made utilizing the DNA sequence data. The first oligonucleotide primer contained a BamHI site to facilitate cloning, a stop codon in frame with the tetracycline gene to terminate translation of the tet protein, an E. coli consensus ribosome binding site, seven nucleotide spacer between the rbs and the ATG start codon of the SpeI methylase gene and 19 nucleotides complementary to Sphareotilus species DNA for hybridization:

Primer SpeMexp1:
5'-GTTGGATCCGTTAAGGAGGTTAATACTATGAGT GGCATGCG-3' (SEQ ID NO:11)

The reverse primer was designed to hybridize at the 3' end of the methylase gene and had a SalI site added to facilitate cloning:

Primer SpeMexp2:
5'-CCTGACGTCGACTCATTAAGGAACTACTCCTG-3' (SEQ ID NO:12)

These two primers were used to amplify the SpeI methylase gene from Sphaerotilus species genomic DNA by combining:

10 μl 10× Vent™ reaction buffer
6 μl of 4 mM dNTPs
2 μl (400 ng) Sphaerotilus species genomic DNA
5 μl (10 uM stock) primer SpeMexp1
5 μl (10 uM stock) primer SpeMexp2
4 μl of 100 mM MgSO$_4$ (8 mM Mg$^{++}$ final concentration)
68 μl dH$_2$O
0.8 μl (1.6 units) Vent™polymerase (2 unit/μl stock)

and amplifying at 95° C. for 3 minutes for 1 cycle, followed by 4 cycles of 95° C. for 30 seconds, 560C for 30 seconds, 72° C. for 1 minute, followed by 20 cycles of 95° C. for 30 seconds, 65° C. for 30 seconds and 72° C. for 1 minute. 15 ul of the PCR reaction was analyzed by electrophoresis on a 0.8% agarose gel. A band of approximately 1.0 kb was oberved as expected from the DNA sequence data. This band was gel purified and approximately 1 ug of the gel purified DNA was digested with BamHI (20 units) and SalI (20 units) in a final volume of 50 ul in NEB bufferSalI (150 mM NaCl, 10 mM Tris-HCl, 10 mM MgCl$_2$, 1 mM dithiothritol pH 7.9 @ 25° C.). This reaction was incubated at 37° C. for 1 hour and was terminated by heating at 78° C. for 20 minutes. 5 ul (100 ng) of the digested DNA was ligated to 100 ng of the vector pSYX20, previously cleaved with BamHI and SalI and agarose gel purified, using 400 U T4 DNA ligase in 20 ul volume at 16° C. for 2 hours. 10 ul of the ligation mixture was transformed into E. coli strain ER2427 and plated on L-broth plates containing 50 ug/ml kanamycin for individual colonies. 12 individual colonies were propagated in 10 ml of L-broth containing 50 ug/ml kanamycin at 37° C. with shaking overnight, and plasmids were isolated by performing minipreps. 5 of the 12 individuals examined contained a 1 kb insert which could be excised by cutting with BamHI and SalI. To test whether these 5 constructs express SpeI methylase activity, the vector Litmus 38 (New England Biolabs, Inc.; Beverly, Mass.), which contains a single SpeI site, was cotransformed with the 5 putative pSYX20SpeI methylase clones into E. coli strain 2427 and plated on L-broth plates containing 100 ug/ml ampicillin and 50 ug/ml kanamycin. Individual transformants were isolated by performing minipreps and digested with SpeI and ScaI. The plasmids from all of the 5 methylase clones were fully protected from SpeI digestion as shown by the absence of an 801 bp ScaI/SpeI fragment. One such clone, designated as pSYX20SpeIM9 was used for endonuclease expression.

B. Endonuclease cloning: The restriction endonuclease gene was expressed by inserting the gene into a expression vector, pRRS, directly downstream of a strong inducible promotor (PlacUV5) and a strongly recognized ribosome binding site. To accomplish this, two oligonucleotide primers were made utilizing the DNA sequence data. The forward oligonucleotide primer contained a NsiI site to facilitate cloning, a stop codon in frame with the lacZ gene to terminate translation of the lacZ protein, a strongly recognized ribosome binding site, seven nucleotide spacer between the rbs and the ATG start codon of the SpeI endonuclease gene and 21 nucleotides complementary to Sphaerotilus species DNA for hybridization:

Primer SpeIRexp1:
5'-GGTTATGCATTTAAGGAGGTTTAACATATGTCA ATCGATCCCAA CAAG-3' (SEQ ID NO:13)

The reverse primer was designed to hybridize to *Sphaerotilus* species DNA at the 3' end of the SpeI endonuclease gene. It contained a BamHI restriction site to facilitate cloning and a change of the stop codon from TGA to TAA. Primer SpeIRexp2:

5'-GGTGGATCCGTCGACTTACCGGACAACAGGAA ATTTTC 3' (SEQ ID NO:14)

These two primers were used to amplify the SpeI endonuclease gene from *Sphaerotilus* species genomic DNA by combining:

10 ul 10× Vent™ reaction buffer 6 ul of 4 mM dNTPs 2 ul (400 ng) *Sphaerotilus* species genomic DNA 5 ul (10 uM stock) primer SpeIRexp1

5 ul (10 uM stock) primer SpeIRexp2

Figure 4:
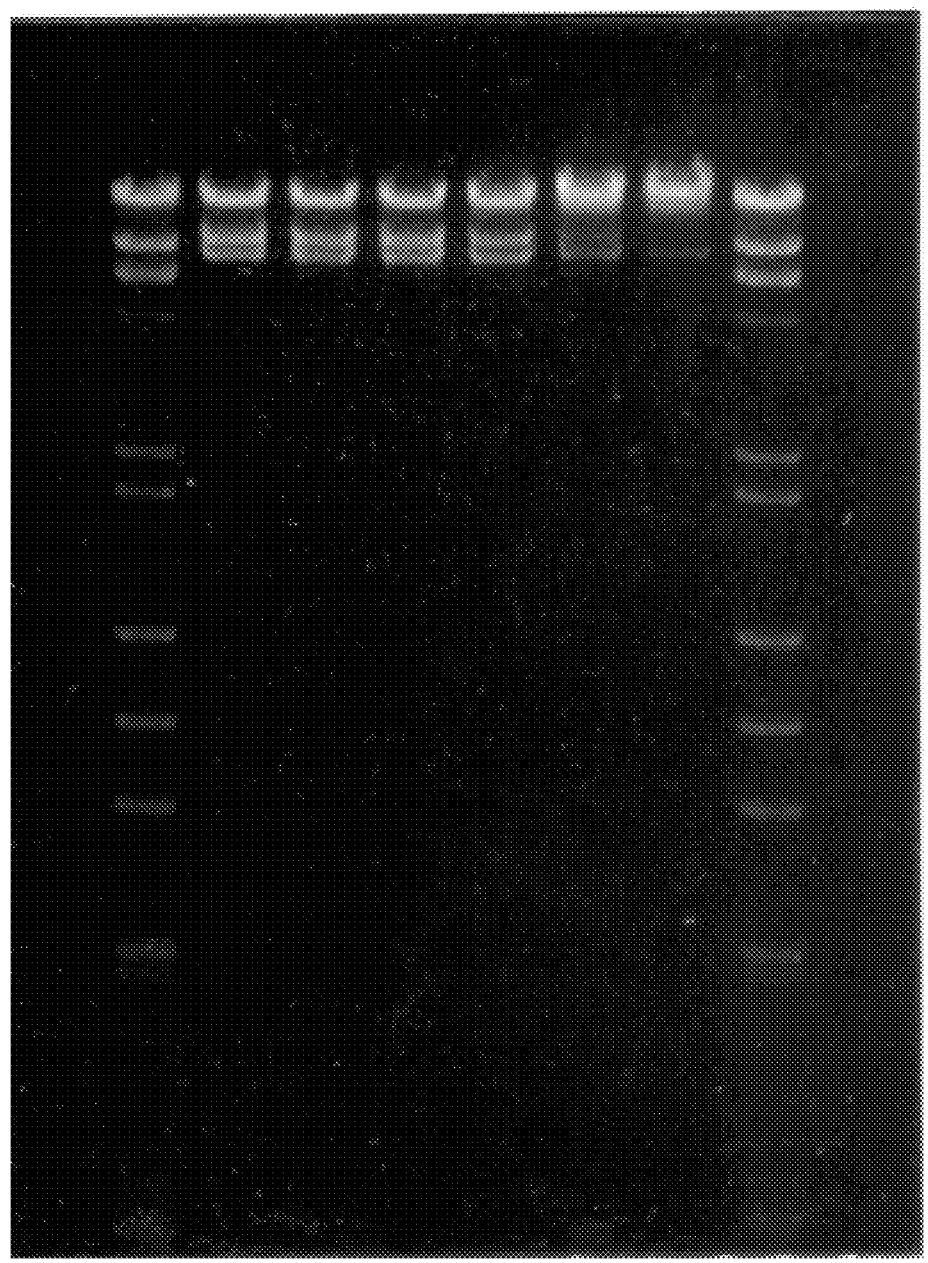
FIG. 4 is a photograph of an agarose gel demonstrating SpeI restriction endonuclease activity in cell extracts of *E. coli* ER2427 carrying the SpeI endonuclease on the pRRS derived plasmid pSpeIR7 and the SpeI methylase on the pSYX20 derived plasmid pSYX20SpeIM9. 1.8 grams of cell paste was suspended in 25 ml of sonication buffer (20 mM Tris-HCl, 1 mM dithiothreitol, 0.1 mM EDTA, pH 7.5), broken by sonication, and clarified by centrifugation. Dilutions of the extract were used to digest 1 μg of T7 DNA per 50 μl reaction volume in 1× NEBuffer 2. The reactions were incubated at 37° C. for 1 hour and the digestion products were separated by agarose gel electrophoresis. Lanes 1 and 8: HindIII-λ+HaeIII-φX174 size standard; lane 2: $2 \times 10^{-3}$ μl crude extract; lane 3: $1 \times 10^{-3}$ μl crude extract; lane 4: $5 \times 10^{-4}$ μl crude extract; lane 5: $2.5 \times 10^{-4}$ μl crude extract; lane 6: $1.25 \times 10^{-4}$ μl crude extract; lane 7: $6.25 \times 10^{-5}$ μl crude extract.

4 ul of 100 mM MgSO$_4$ 66 ul dH$_2$O 0.6ul (1.2 units) Vent™ polymerase (2 unit/ul stock) and amplifying at 95° C. for 3 minutes for 1 cycle, followed by 4 cycles of 95° C. for 30 seconds, 60° C. for 20 seconds, 72° C. for 45 seconds, followed by 20 cycles of 95° C. for 30 seconds, 65° C. for 20 seconds and 72° C. for 45 seconds. The amplification product of approximately 600 bp was gel purified, cleaved with NsiI and BamHI, phenol-chloroform extracted, precipitated, resuspended in TE and ligated into pRRS vector previously cleaved with PstI and BamHI and gel purified. The ligation reaction was transformed into *E. coli* strain ER2427 previously modified with the SpeI methylase gene construct pSYX20SpeIM9. Out of 6 individual transformants analyzed, all expressed SpeI endonuclease activity. One of these clones, pSpeIR7, was selected for producing the SpeI endonuclease and given the strain designation of NEB #1038. A titration of the SpeI restriction endonuclease activity produced from crude extracts of NEB #1038 is shown in FIG. 4. The enzyme titer was approximately 2×10$^7$ units/g of cells.

10. The SpeI restriction endonuclease may be produced from NEB #1038 by propagation to mid-log phase in a fermenter containing L-broth medium with ampicillin (100 µg/ml) and kanamycin (50 µg/ml). The culture is induced by the addition of IPTG to a final concentration of 0.3 mM and allowed to continue growing for 16 hours. The cells are harvested by centrifugation and may be stored at −70° C. or used immediately.

11. Purification of the SpeI restriction endonuclease from NEB #1038 can be accomplished by a combination of standard protein purification techniques, such as affinity-chromatography or ion-exchange chromatography, as outlined in step 6 above. The SpeI restriction endonuclease obtained from this purification is substanially pure and free of non-specific endonuclease and exonuclease contamination.

A sample of the *E. coli* containing both pSYX20SpeIM9 and pSpeIR7 (NEB#1038) has been deposited under the terms and conditions of the Budapest Treaty with the American Type Collection on Mar. 20, 1997 and received ATCC Accession Number 98366.

What is claimed is:

1. Isolated DNA coding for the SpeI restriction endonuclease, wherein the isolated DNA is obtainable from *Sphaerotilus* species.

2. A recombinant DNA vector comprising a vector into which a DNA segment coding for the SpeI restriction endonuclease has been inserted.

3. Isolated DNA coding for the SpeI restriction endonuclease and methylase, wherein the isolated DNA is obtainable from ATCC No. 98366.

4. A cloning vector which comprises the isolated DNA of claim 3.

5. A host cell transformed by the cloning vector of claims 2 or 4.

6. A method of producing a SpeI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO. : 5,945,326
DATED : August 31, 1999
INVENTOR(S) : Richard D. Morgan, et. al.

Page 1 of 2

It is certified that error appears in the above-identified patent and that said Letters Patent is hereby corrected as shown below:

<u>In the Title</u>

Replace "SPEL" with --SpeI--

| | |
|---|---|
| Column 1, line 2 | replace "SPEL" with --SpeI-- |
| Column 6, line 61 | replace "PRRS" with --pRRS-- |
| Column 7, line 11 | replace "Sphaerotilus" with --*Sphaerotilus*-- |
| Column 13, lines 10-11 | replace "HCTVKPLPLMLKLVGMMVPPFANNIVLDPFAGSGTTLVAAKQLGLTYLGIE" with --HCTVKPLPLMLKLVGMMVPPFANNIVLDPFAGSGTTLVAAKQLGLTYLGIE-- |
| Column 13, lines 17-18 | replace "GDCRELLAKIPAASIAACITDPPY" with --GDCRELLAKIPAASIAACITDPPY-- |
| Column 15, line 23 | replace "(Met)-Ser-1le-Asp" with --(Met)-Ser-Ile-Asp-- |
| Column 15, line 24 | replace "Ala-Leu-Asp-Ala-1le-Leu" with --Ala-Leu-Asp-Ala-Ile-Leu-- |
| Column 16, line 16 | replace "560C" with --56°C-- |

UNITED STATES PATENT AND TRADEMARK OFFICE
CERTIFICATE OF CORRECTION

PATENT NO.   : 5,945,326
DATED        : August 31, 1999
INVENTOR(S)  : Richard D. Morgan, et. al.

It is certified that error appears in the above-identified patent and that said Letters Patent is hereby corrected as shown below:

| | | |
|---|---|---|
| Column 1, line 41 | replace "molecule" with | --molecules-- |
| Column 3, line 24 | replace "are" with | --is-- |
| Column 4, line 16 | replace "methlase" with | --methylase-- |
| Column 5, line 57 | replace "methods" with | --Methods-- |
| Column 6, lines 27 | replace "putativeSpeI" with | --putative SpeI-- |
| Column 7, line 44 | replace "acids" with | --acid-- |
| Column 7, line 62 | replace "1991)" with | --(1991)-- |
| Column 8, line 40 | replace "1346" with | --346-- |
| Column 15, line 66 | replace "a" with | --an-- |
| Column 16, line 53 | replace "a" with | --an-- |
| Column 16, line 58 | replace "a" with | --an-- |

Signed and Sealed this

Seventh Day of March, 2000

Attest:

Attesting Officer

Q. TODD DICKINSON

Commissioner of Patents and Trademarks

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

CCAACTAGTT GG                                            12

(2) INFORMATION FOR SEQ ID NO:2:

(i) SEQUENCE CHARACTERISTICS:
      (A) LENGTH: 152 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:2:

CACTGCACCG TAAAGCACTT CCGTTGATGC TTAAGCTTGT GGGGATGATG GTTCCGCCTT    60

TTGCAAACAA CATCGTACTT GACCCGTTTG CTGGTTCGGG TACCACGCTT GTGGCCGCAA    120

AGCAGCTCGG TCTCACTTAT CTTGGTATCG AG    152

(2) INFORMATION FOR SEQ ID NO:3:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
His Cys Thr Val Lys Pro Leu Pro Leu Met Leu Lys Leu Val Gly Met
 1               5                  10                  15

Met Val Pro Pro Phe Ala Asn Asn Ile Val Leu Asp Pro Phe Ala Gly
                20                  25                  30

Ser Gly Thr Thr Leu Val Ala Ala Lys Gln Leu Gly Leu Thr Tyr Leu
            35                  40                  45

Gly Ile Glu
    50
```

(2) INFORMATION FOR SEQ ID NO:4:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

```
GGAGACTGCC GCGAACTACT GGCGAAAATC CCTGCAGCAT CTATCGCGGC ATGCATTACA    60

GACCCACCCT AC                                                       72
```

(2) INFORMATION FOR SEQ ID NO:5:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Gly Asp Cys Arg Glu Leu Leu Ala Lys Ile Pro Ala Ala Ser Ile Ala
 1               5                  10                  15

Ala Cys Ile Thr Asp Pro Pro Tyr
                20
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

```
GTTGGATCCG AGCAGTCTCA CCG                                           23
```

(2) INFORMATION FOR SEQ ID NO:7:

(i) SEQUENCE CHARACTERISTICS:
        (A) LENGTH: 25 base pairs (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GTTCTGCAGC TTTGTCAATG CCGAG                                             25

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

GAACTATCAA GAGTACTGGC TC                                                22

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

GTTGGATCCT CTGCTCGAGC GAGGGGTG                                          28

(2) INFORMATION FOR SEQ ID NO:10:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Ser Ile Asp Pro Asn Lys Leu Asn Ser Ala Leu Asp Ala Ile Leu
 1               5                  10                  15

Glu Gly Tyr Xaa Gly Glu Phe Ser Asn Lys Val Tyr
            20                  25

(2) INFORMATION FOR SEQ ID NO:11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

GTTGGATCCG TTAAGGAGGT TAATACTATG AGTGGCATGC G                           41

(2) INFORMATION FOR SEQ ID NO:12:

(i) SEQUENCE CHARACTERISTICS:
        (A) LENGTH: 32 base pairs
        (B) TYPE: nucleic acid (C) STRANDEDNESS: single
        (D) TOPOLOGY: linear (ii) MOLECULE TYPE: Genomic DNA (xi) SEQUENCE DESCRIPTION: SEQ ID NO:12:

CCTGACGTCG ACTCATTAAG GAACTACTCC TG                                    32

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

GGTTATGCAT TTAAGGAGGT TTAACATATG TCAATCGATC CCAACAAG                   48

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

GGTGGATCCG TCGACTTACC GGACAACAGG AAATTTTC                              38